(12) United States Patent
Komnick

(10) Patent No.: US 9,604,186 B1
(45) Date of Patent: Mar. 28, 2017

(54) AUTOMATED MULTICHANNEL MEDIA DISPENSER

(71) Applicant: Dow AgroSciences LLC, Indianapolis, IN (US)

(72) Inventor: Justin Komnick, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 746 days.

(21) Appl. No.: 13/872,352

(22) Filed: Apr. 29, 2013

Related U.S. Application Data

(60) Provisional application No. 61/641,001, filed on May 1, 2012.

(51) Int. Cl.
*B01F 15/02* (2006.01)
*B01F 13/10* (2006.01)
*B01F 15/04* (2006.01)

(52) U.S. Cl.
CPC ...... *B01F 15/0441* (2013.01); *B01F 13/1066* (2013.01); *B01F 15/0203* (2013.01)

(58) Field of Classification Search
CPC .............. B01F 13/1055; B01F 13/1058; B01F 13/1066; B01F 15/0203; B01F 15/042; B01F 15/0441
USPC ........................... 366/273, 274, 177.1, 178.1
See application file for complete search history.

(56) References Cited

U.S. PATENT DOCUMENTS

| | | | | |
|---|---|---|---|---|
| 3,575,605 A | * | 4/1971 | Conner ................. | H03K 17/725 307/29 |
| 3,901,656 A | * | 8/1975 | Durkos ................. | G01N 35/025 422/64 |
| 3,993,218 A | * | 11/1976 | Reichenberger ......... | B67D 1/04 222/129.4 |
| 4,366,119 A | * | 12/1982 | Takeuchi ............. | G01N 35/021 422/561 |
| 4,753,370 A | * | 6/1988 | Rudick ................ | B67D 1/0051 222/105 |
| 4,871,262 A | * | 10/1989 | Krauss ................ | B01F 13/1055 222/135 |

(Continued)

FOREIGN PATENT DOCUMENTS

| | | |
|---|---|---|
| JP | 2002205797 | 7/2002 |
| RU | 2372977 | 11/2009 |

OTHER PUBLICATIONS

MicroFlo™ Select Dispenser from BioTek Instruments, Biocompare.com, http://www.biocompare.com/ProductDetails/872122/MicroFloSelect-Dispenser.html, Dec. 15, 2011, 2 pgs.

*Primary Examiner* — Tony G Soohoo
(74) *Attorney, Agent, or Firm* — Eric J. Kraus; Faegre Baker Daniels LLP

(57) ABSTRACT

An apparatus and method for preparing a plant tissue medium are disclosed, the method comprising preparing a plurality of compounds in vessels; positioning a dispensing unit including a plurality of nozzles in communication with the plurality of vessels over an interior of a mixing container; dispensing predetermined amounts of at least one of the liquid compounds through one of the plurality of nozzles into the mixing container wherein the predetermined amounts are controlled by an electronic controller; positioning the dispensing unit in a second position; and sterilizing the mixing container containing the dispensed liquid compounds.

12 Claims, 7 Drawing Sheets

(56) References Cited

U.S. PATENT DOCUMENTS

| | | | |
|---|---|---|---|
| 5,389,339 A * | 2/1995 | Petschek | G01N 35/1002 422/116 |
| 6,000,837 A * | 12/1999 | Randsborg | B01F 13/1055 366/141 |
| 6,988,518 B2 * | 1/2006 | Rackers | G01N 35/109 141/1 |
| 7,383,966 B2 | 6/2008 | Zisel | |
| 7,395,134 B2 | 7/2008 | Bartholomew et al. | |
| 7,559,346 B2 | 7/2009 | Herrick et al. | |
| 7,562,680 B2 | 7/2009 | Khoo et al. | |
| 7,934,622 B2 | 5/2011 | House et al. | |
| 7,967,037 B2 | 6/2011 | Foster et al. | |
| 8,186,872 B2 * | 5/2012 | Bartholomew | G07F 11/165 366/273 |
| 2007/0000947 A1 | 1/2007 | Lewis et al. | |
| 2007/0056989 A1 | 3/2007 | Adema | |
| 2010/0227387 A1 * | 9/2010 | Safar | B01L 3/5082 435/289.1 |
| 2010/0242497 A1 | 9/2010 | Bertone | |
| 2013/0017621 A1 * | 1/2013 | Kaminski | B01F 11/0074 436/180 |

* cited by examiner

AUTOMATED MULTICHANNEL MEDIA DISPENSER

CROSS-REFERENCE TO RELATED APPLICATIONS

This application claims the benefit of U.S. Provisional Application Ser. No. 61/641,001, filed May 1, 2012, the entire disclosure of which is expressly incorporated herein by reference.

FIELD

The present invention relates to methods and apparatus for dispensing liquid media and in particular to methods for dispensing plant tissue culture media.

BACKGROUND

Plant tissue culture techniques are used to reproduce plants from an initial tissue sample, or explant. Explants are cultured in a nutrient media containing nutrients for plant growth.

Media for tissue cultures are prepared according to recipes. Each recipe is composed of one or more ingredient compounds. Typical ingredient compounds include carbohydrates, vitamins, pH buffers, plant growth hormones, antibiotics, selection agents, and water. These ingredients are often liquid, or dehydrated powder that can be dissolved or suspended in water and delivered as a liquid.

Manual preparation of a recipe can be time consuming as each ingredient compound is prepared, measured, and added individually. Manual preparation decreases process efficiency and allows for the introduction of human error during ingredient measuring and assembly of media components.

SUMMARY

In an exemplary embodiment of the present disclosure, a multichannel dispenser for liquid media is provided. In one embodiment, the dispenser includes a plurality of vessels and a dispensing unit including a plurality of dispensing nozzles. For each vessel, transfer tubing transfers a liquid compound ingredient from the vessel to a dispensing nozzle attached to the dispensing unit. A pump transfers each compound through the transfer tubing from the vessel and dispenses the liquid through the dispensing nozzle into a mixing container. In another embodiment, at least one vessel includes a stir bar and is positioned on a stir plate. In still another embodiment, the mixing container is formed from a portion of a mediaclave.

In another exemplary embodiment of the present disclosure, a method of preparing a tissue media is provided. In one embodiment, the method includes moving a dispensing unit containing a plurality of dispensing nozzles into a first position over a mixing container. A predetermined amount of each of a plurality of liquid compounds is dispensed from a plurality of vessels through the dispensing nozzles into the mixing container. A plurality of pumps attached to an electronic controller control the amount of each compound dispensed. The dispensing unit is moved to a second position not over the mixing container and held in the second position by a swing arm attached to the dispensing unit. A lid is closed on the mixing container and the dispensed liquids inside are subjected to an autoclave cycle.

The above mentioned and other features of the invention, and the manner of attaining them, will become more apparent and the invention itself will be better understood by reference to the following description of embodiments of the invention taken in conjunction with the accompanying drawings.

DETAILED DESCRIPTION OF THE DRAWINGS

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to the preparation of liquid media for tissue samples, it should be understood that the features disclosed herein may have application to the preparation of other types of samples.

Figure 1:
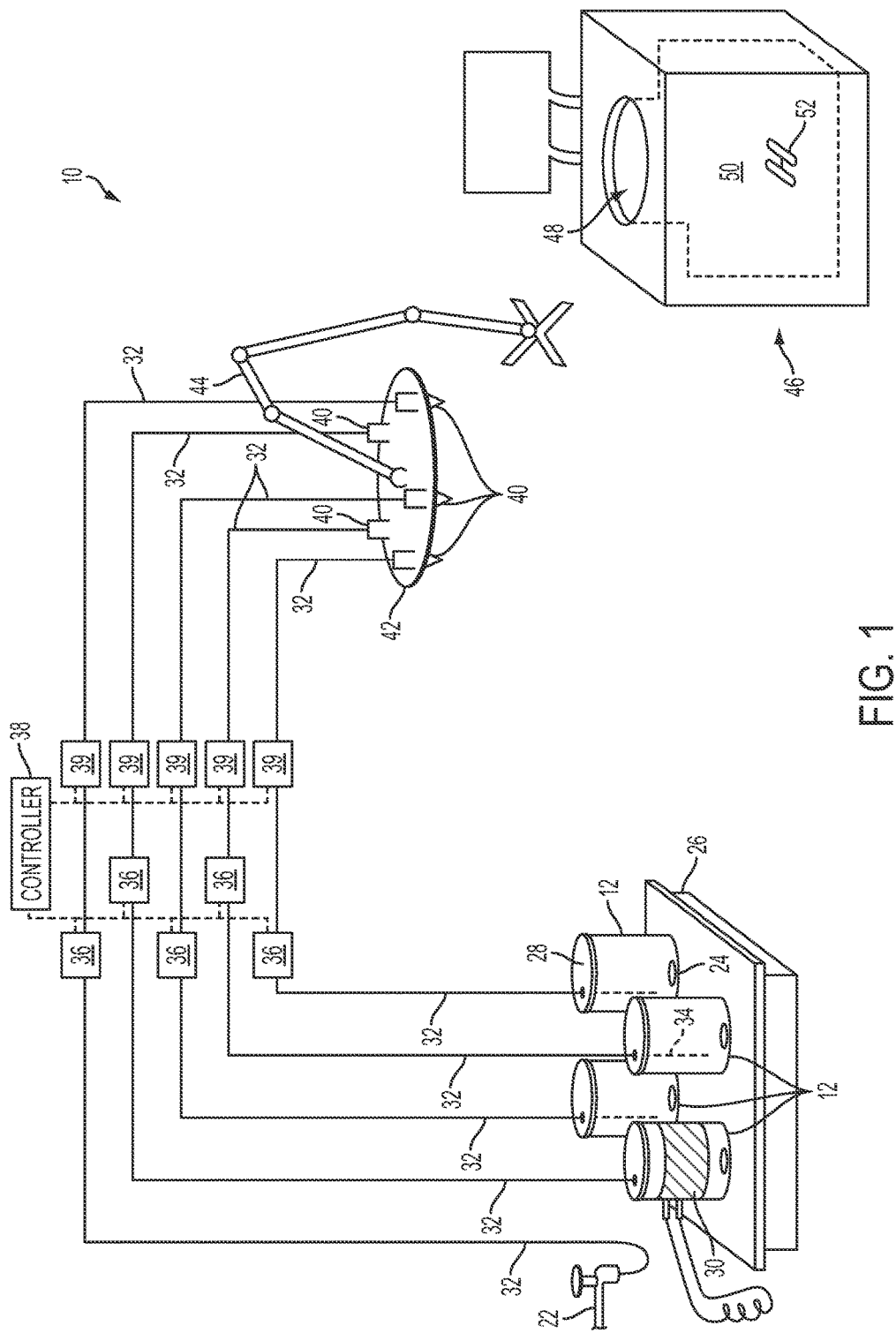
FIG. 1 illustrates an exemplary embodiment of a multichannel media dispenser.

Referring to FIG. 1, an exemplary multichannel media dispenser 10 is illustrated. Dispenser 10 includes a plurality of vessels 12. Although four vessels 12 are illustrated in FIG. 1, more or fewer vessels may be utilized. Each vessel 12 contains a compound 14, 16, 18, 20. Exemplary compounds include liquids, liquids with dissolved solids, liquids with suspensions, and other suitable flowable products. More or fewer compounds may be used, depending on the recipe for media being prepared. In one embodiment, a single vessel is used for each compound in the recipe, although multiple vessels containing the same media may also be used. In one embodiment, from about six to about twelve vessels containing liquid compounds are provided. In one embodiment, from about ten to about fifteen vessels of frequently used liquid compounds are provided.

The composition of compounds 14, 16, 18, 20 depends on the recipe being prepared. In one illustrative embodiment, at least one of compounds 14, 16, 18, 20 contains a carbohydrate, a vitamin source, a pH buffer, a hormone solution, an antibiotic solution, or a selection agent. In another embodiment, at least one of compounds 14, 16, 18, 20 is water. In still another embodiment, water is provided to dispenser 10 from water source 22. The water source 22 includes a water purification system in one embodiment.

In one embodiment, at least one of plurality of vessels 12 includes a stir bar 24 and is positioned on a stir plate 26. In one embodiment, stir bar 24 is magnetic and rotates in response to stir plate 26. In another embodiment, each vessel 12 containing a stir bar 24 is positioned on an individual stir plate 26. In still other embodiments, stir plate 26 is a stir platform containing multiple positions for at least some of the plurality of vessels 12.

In one example embodiment, at least one of the plurality of vessels 12 includes vessel cap 28. The vessel and corresponding vessel cap 28 cooperate to surround the liquid provided in the vessel. In still another example embodiment, at least one of the plurality of vessels 12 includes a cooling or heating jacket 30 to maintain the temperature of the compound in vessel 12.

One end of a piece of transfer tubing 32, shown as tubing inlet 34 in FIG. 1, is positioned in each of the plurality of vessels 12. Tubing inlet 34 is positioned to receive a liquid from a vessel 12, such as compounds 14, 16, 18, 20, or water from water source 22. Pumps 36 controlled by controller 38 transfer the liquid through transfer tubing 32. Each piece of transfer tubing 32 is attached to a dispensing nozzle 40 on dispensing unit 42. Dispensing unit 42 is attached to swing arm 44 that holds dispensing unit 42 in position. In one exemplary embodiment, swing arm 44 is an articulating arm including a plurality of segments and joints.

Compounds 14, 16, 18, 20 are dispensed through dispensing nozzles 40 into mixing vessel 46. Mixing vessel 46 includes a top opening 48 through which compounds 14, 16, 18, 20 are dispensed into an interior 50 of vessel 46. In one embodiment, mixing vessel 46 is part of an autoclave. In one embodiment, mixing vessel 46 is an inner vessel of a media preparator, such as Systec MediaPrep available from Systec GmbH, Wettenberg, Germany. In one embodiment, mixing vessel includes a mixing element 52. In an exemplary mixing element 52 is a magnetic stir bar.

Figure 2:
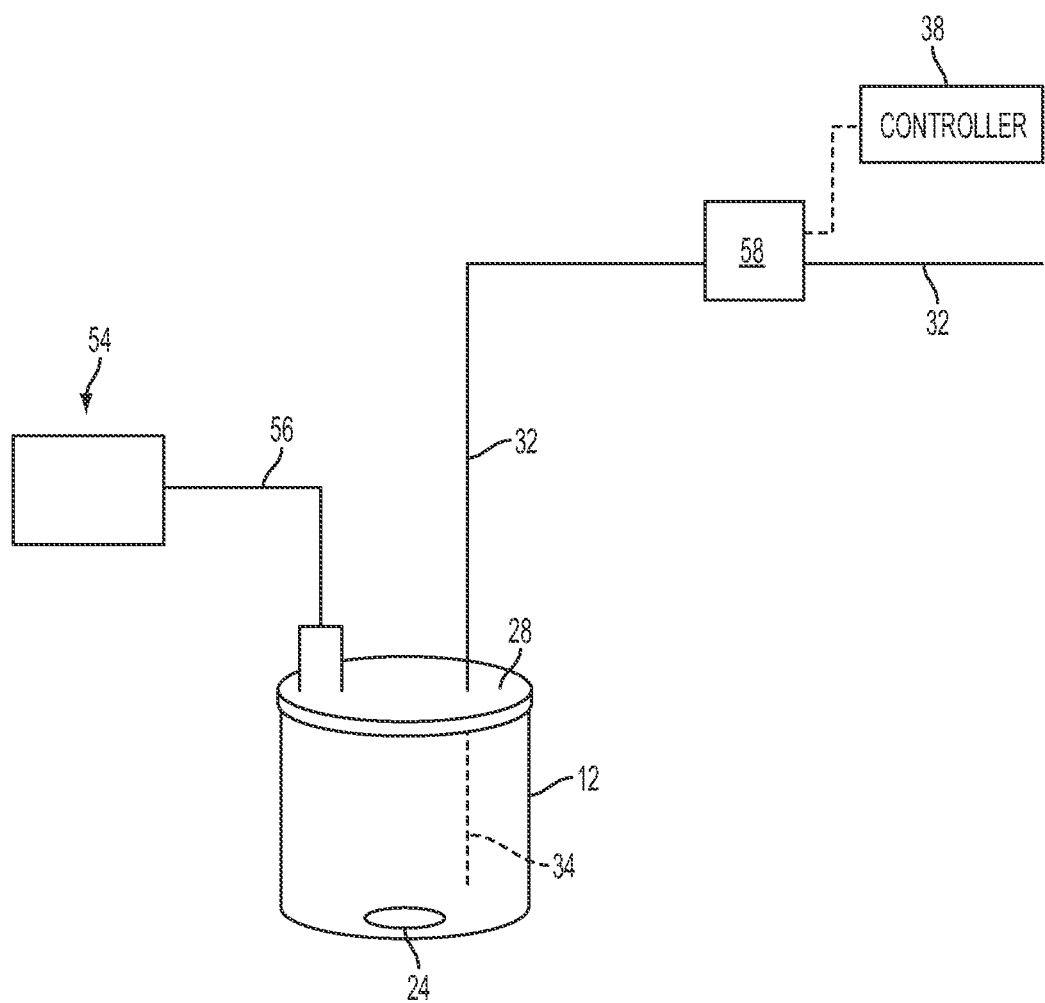
FIG. 2 illustrates an exemplary pressure system attached to one vessel of another exemplary embodiment of a multichannel media dispenser.

Referring to FIG. 2, a portion of an exemplary embodiment of a multichannel media dispenser is illustrated. FIG. 2 shows vessel 12 connected to positive pressure system 54. Positive pressure system 54 provides pressurized air or other gas to the plurality of vessels 12 through pressurized tubing 56 attached to vessel caps 28. Controller 38 controls the status of valves 58. When valves 58 are open, liquid flows through transfer tubing 32. When valves 58 are closed, liquid does not flow through transfer tubing 32. Transfer tubing 32 connects to dispensing nozzles 40 attached to dispensing unit 42 as in the exemplary embodiment shown in FIG. 1.

Returning to FIG. 1, in one embodiment, a water source 22 is connected by transfer tubing 32 to a dispensing nozzle 40 on dispensing unit 42. Controller 38 sends an on or off signal to water source 22. When water source 22 receives an on signal, water source 22 provides water through transfer tubing 32 to dispense through dispensing nozzle 40. When water source 22 receives an off signal, water source 22 stops providing water through transfer tubing 32 to dispense through dispensing nozzle 40. An exemplary water source 22 is a Milli-Q lab water purification system available from EMD Millipore Corporation, Billerica, Mass.

Other pump or pressure systems are also contemplated. In one embodiment, pumps 36 are peristaltic or roller pumps. Peristaltic or roller pumps, used with flexible transfer tubing 32, allow compounds 14, 16, 18, 20 to be transferred through tubing 32 without being contacted by the pump. In another embodiment, pumps 36 are gear or piston pumps. Gear or piston pumps may be used where the media prepared from the compounds is sterilized through use of an autoclave or other method. Other suitable pumps or pressure systems may also be used.

In one embodiment, dispenser 10 includes controller 38 controlling at least one pump 36 and at least one valve 58. The controller 38 may control one or more of at least one pump and water source 22. Other combinations of pumps, valves, and pressure systems are also contemplated.

In one embodiment, a flow meter 39 is associated with each pump 36 or valve 58. Exemplary flow meters 39 include paddle wheel, optical sensor, wafer, and vortex generator type flow matters. Other suitable flow meters may be used. In the exemplary embodiment illustrated in FIG. 1, each flow meter 39 is operably connected with controller 38. Controller 38 uses output from flow meter 39 to determine the amount of each ingredient dispensed. When a predetermined amount of liquid has been dispensed, controller 38 signals pump 36, valve 58, or water source 22 to stop the flow of fluid through transfer tubing 32.

In one embodiment, pumps 36 or valves 58 may be calibrated by measuring the volume of liquid dispensed over a period of time at a set pump speed or valve position. A predetermined amount of liquid may then be dispensed by activating the pump 36 at the same speed or opening the valve 58 to the same position for the amount of time needed to dispense that amount of liquid.

Figure 3:
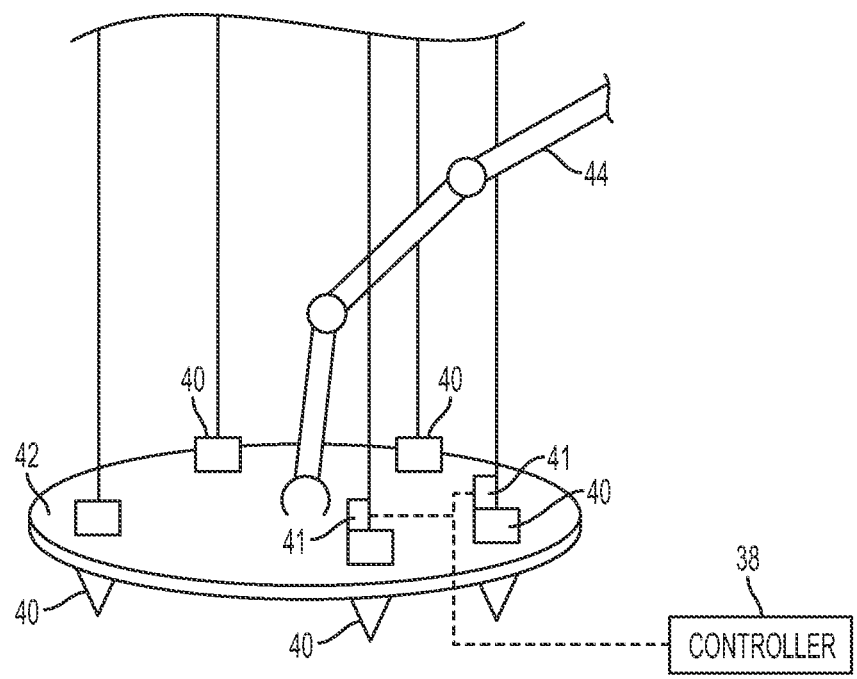
FIG. 3 illustrates an exemplary dispensing unit.

Referring to FIG. 3, an exemplary dispensing unit 42 is illustrated. A plurality of dispensing nozzles 40 are attached to dispensing unit 42. In the illustrated embodiment, dispensing nozzles 40 extend through dispensing unit 42. Transfer tubing attaches to the portion of dispensing nozzle 40 above dispensing unit 42 and compounds 14, 16, 18, 20 are dispensed through dispensing nozzles 40 into mixing element 52.

In one embodiment, at least one of dispensing nozzles 40 includes a nozzle valve 41 in communication with controller 38. Controller 38 controls the status of the respective nozzle valves 41. When a nozzle valve 41 is open, liquid flows through the corresponding nozzle 40. When the nozzle valve 41 is closed, liquid does not flow through the corresponding nozzle 40. In one embodiment, controller 38 opens nozzle valves 41 when pump 36, valve 58, or water source 22 is transferring fluid through transfer tubing 32 and controller 38 closes nozzle valves 41 when pump 36, valve 58, or water source 22 is not transferring fluid through transfer tubing 32 to prevent additional fluid from draining from transfer tubing 32 into mixing vessel 46. In one embodiment, nozzle valves 41 are solenoid valves. In one embodiment, nozzle valves 41 include a piezoelectric element to open and close a valve element in nozzle valve 41. Other suitable valves may also be used.

In one embodiment, dispensing nozzles 40 are spaced evenly around the edge of dispensing unit 42. Other suitable arrangements may also be used, including but not limited to grouping nozzles by ingredient type, placing pairs of nozzles together, and leaving spaces for additional nozzles to be added. In one embodiment, dispensing unit 42 is circular in shape to match the circular shape of the top opening 48 of mixing vessel 46. Other suitable shapes may also be used, including but not limited to linear, triangular, rectangular, and octagonal.

In one exemplary embodiment, dispensing unit 42 is attached to swing arm 44. Swing arm 44 supports dispensing unit 42. The use of flexible tubing for transfer tubing 32 allows swing arm 44 to move dispensing unit 42 between multiple positions.

Figure 4:
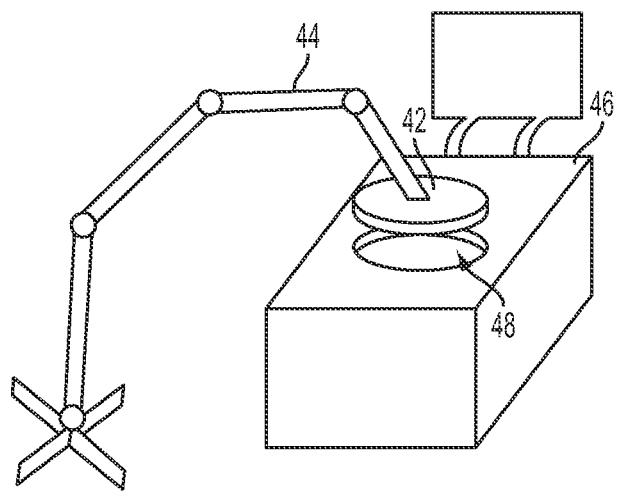
FIG. 4 illustrates the exemplary dispensing unit of FIG. 3 in an exemplary first position over the mixing container.
Figure 5:
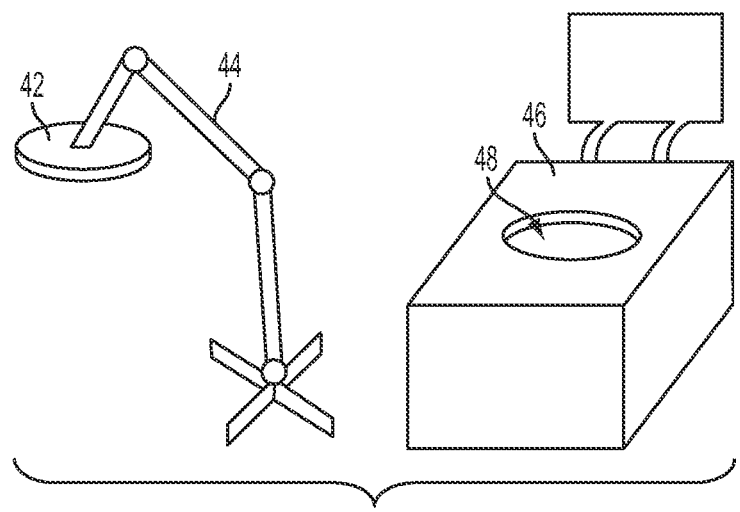
FIG. 5 illustrates the exemplary dispensing unit of FIG. 3 in an exemplary second position not over the mixing container.

Referring to FIGS. 4 and 5, the exemplary dispensing unit 42 is illustrated in an exemplary first position and an exemplary second position.

In FIG. 4, dispensing unit 42 is shown in an exemplary first position. In the illustrated first position, dispensing nozzles 40 are positioned to deliver compounds 14, 16, 18, 20 to the interior 50 of mixing vessel 46. In one exemplary embodiment, dispensing unit 42 is supported by swing arm 44 in the first position. In another exemplary embodiment, dispensing unit 42 is supported by mixing vessel 46.

In FIG. 5, dispensing unit 42 is shown in an exemplary second position. In the illustrated second position, dispensing nozzles 40 are not positioned above mixing vessel 46. Other locations for a second position besides that illustrated in FIG. 5 are contemplated, such as nearer to or further away from mixing vessel 46, or above or below the plane of top opening 48 of mixing vessel 46. In an exemplary embodiment, when dispensing unit 42 is in the second position, lid 60 can be attached to mixing vessel 46 to cover top opening 48.

In one embodiment, the mixing vessel 46 is moved to provide the first position in which the dispensing unit 42 is over top opening 48 of mixing vessel 46 and the second position in which the dispensing unit 42 is not over the top opening 48 of mixing vessel 46. In one embodiment, both the mixing vessel 46 and the dispensing unit 42 are moved to provide the first position in which the dispensing 42 unit is over top opening 48 of mixing vessel 46 and the second position in which the dispensing unit 42 is not over the top opening 48 of mixing vessel 46.

The amount of each ingredient compound 14, 16, 18, 20 dispensed through dispensing nozzles 40 to the mixing vessel 46 is controlled by controller 38. In one embodiment, controller 38 controls the amount of liquid passing through transfer tubing 32 by controlling the pumps 36. In one embodiment, controller 38 controls the amount of liquid passing through transfer tubing 32 by controlling the status of valves 58. In one embodiment, water source 22 provides a constant flow rate of water when turned on and controller 38 controls the amount of water passing through transfer tubing 32 by turning on or off water source 22. In one exemplary embodiment, controller 38 controls the amount of liquid passing through transfer tubing 32 by controlling one or more of pumps 36, valves, and water source 22.

In one embodiment, controller 38 dispenses a predetermined amount of a first compound 14 through a dispensing nozzle 40 before dispensing a predetermined amount of a second compound 16 through a second dispensing nozzle 40. In one embodiment, controller 38 dispenses a predetermined amount of a first compound 14 through a dispensing nozzle 40 while dispensing a predetermined amount of a second compound 16 through a second dispensing nozzle 40. In one embodiment, controller 38 dispenses a predetermined amount of compounds 14, 16, 18, 20 before dispensing water from water source 22. A predetermined amount of water from water source 22 may be dispensed, or an operator may dispense water from water source 22 until a predetermined volume is reached in mixing vessel 46.

Figure 6:
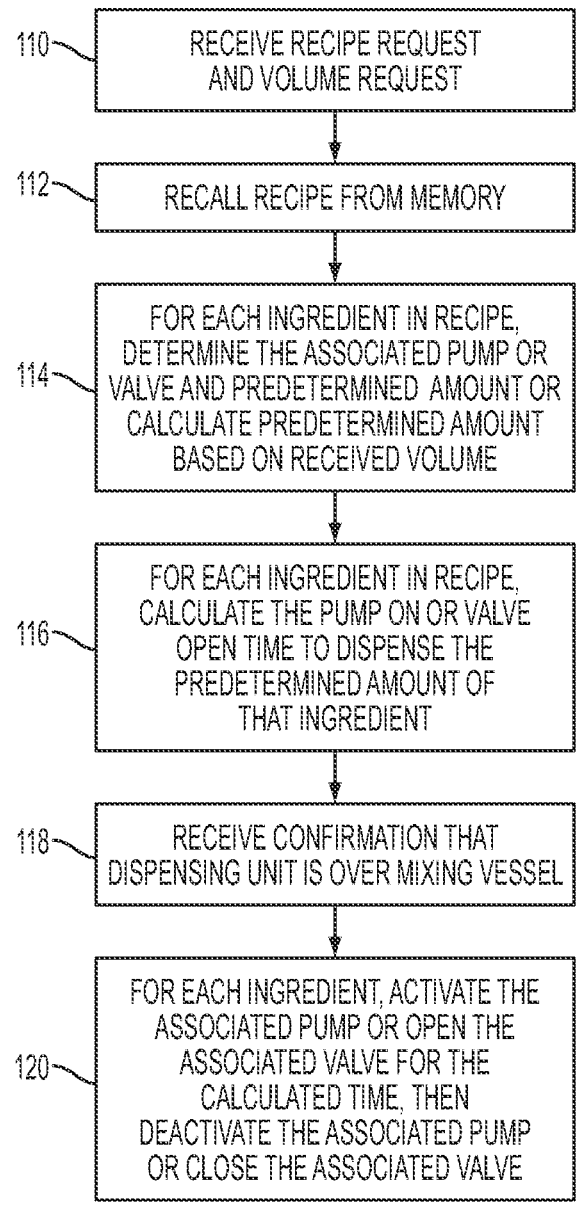
FIG. 6 illustrates an exemplary processing sequence for a controller controlling the pumps or valves of FIG. 1 or 2.

Referring to FIG. 6, an exemplary processing sequence by controller 38 is illustrated. In the exemplary sequence, controller 38 receives a request for a given recipe, as represented by block 110. The recipe may be stored in the memory of controller 38, or it may be input as part of the request. If the recipe is input, it is stored in memory by controller 38 so it may be recalled later. In one example embodiment, the recipe provides predetermined amounts of each ingredient to be used, and the total volume of the recipe can be found by adding the predetermined amount of each ingredient found in the recipe together. In another example embodiment, the recipe provides relative amounts of each ingredient. In this embodiment, a requested volume is input along with the recipe request. Once the request has been received, controller 38 recalls the recipe from its memory, as represented by block 112.

As represented by block 114, for each ingredient in the recalled recipe, controller 38 determines the associated pump or valve for that ingredient. Also as represented by block 114, controller determines the predetermined amount of each ingredient in the recipe. If the predetermined amounts in the recipe are provided as relative amounts of each ingredient, the amount of each ingredient is determined.

As represented by block 116, for each ingredient in the recipe, the pump on time or valve open time to dispense the predetermined amount of each ingredient is calculated by controller 38. The controller then receives confirmation that dispensing unit 42 or dispensing nozzles 40 are above top opening 48 of mixing vessel 50, as represented in block 118. This ensures that the ingredient compounds are dispensed into mixing vessel 50. Confirmation may be provided by an input by a user, or a sensor in either mixing vessel 50 or dispensing unit 42 may provide the confirmation.

As represented by block 120, for each ingredient, controller 38 activates associated pump 36 or an associated valve 58 for the determined time to dispense the predetermined amount of the ingredient compound. Once the determined time has elapsed, controller 38 deactivates associated pump 36 or closes associated valve 58.

In one embodiment, operation of dispenser 10 is controlled by controller 38. Controller 38 may be a single controller or multiple controllers. In the embodiment illustrated in FIG. 7, controller 38 includes a plurality of modules 200. Modules 200 may be implemented as electrical circuits, software being executed by a processing unit, a combination thereof, or any other suitable configuration of hardware, software and/or software enabled hardware.

In one embodiment, controller 38 includes memory. Memory is a computer readable medium and may be a single storage device or may include multiple storage devices, located either locally with controller 38 or accessible across a network. Computer-readable media may be any available media that may be accessed by controller 38 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by controller 38. In one embodiment, controller 38 communicates data, status information, or a combination thereof to a remote device for analysis. In another embodiment, memory may further include operating system software, such as WINDOWS operating system available from Microsoft Corporation of Redmond Wash. Memory further includes communications software if computer system has access to a network, such as a local area network, a public switched network, a CAN network, and any type of wired or wireless network. Any exemplary public switched network is the Internet. Exemplary communications software includes e-mail software, internet browser software. Other suitable software which permit controller 38 to communicate with other devices across a network may be used.

In one exemplary embodiment, dispenser 10 further includes one or more I/O modules which provide an interface between an operator and dispenser 10. Exemplary I/O modules include input members and output members. Exemplary input members include buttons, switches, keys, a touch display, a keyboard, a mouse, and other suitable devices for providing information to controller. Exemplary output devices include lights, a display (such as a touch screen), printer, speaker, visual devices, audio devices, tactile devices, and other suitable devices for presenting information to an operator.

Figure 7:
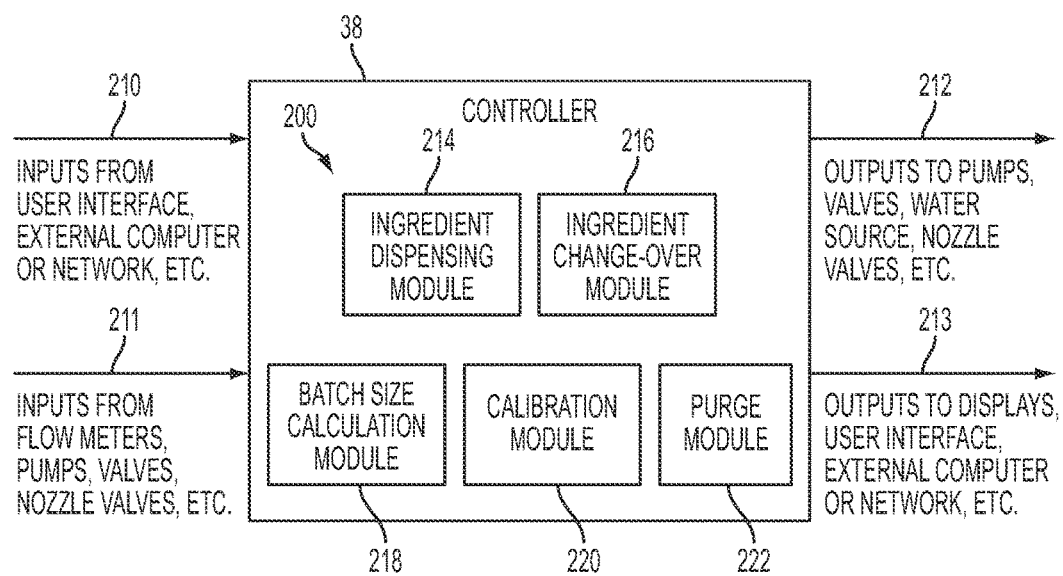
FIG. 7 is a representative view of exemplary controller modules.

Referring to FIG. 7, a representative view of controller 38 is illustrated. Controller 38 includes a variety of modules 200. Controller 38 receives input signals 210, 211. Exemplary input signals 210, 211 include inputs from a user interface, external computers, inputs from flow meters, and feedback from pumps, valves, water sources. Other suitable inputs may also be received. Utilizing modules 200, controller 38 sends output signals 212, 213. Exemplary output signals include output signals 212 to pumps, valves, water sources, and nozzle valves to maintain or change status, and output signals 213 to displays, user interfaces, external computers, or networks. Exemplary modules 200 include, but are not limited to, ingredient dispensing module 214, ingredient change-over module 216, batch size calculation module 218, calibration module 220, and purge module 222.

In one embodiment, controller 38 includes ingredient dispensing module 214. Ingredient dispensing module 214 receives predetermined amounts of each ingredient from a user interface, external computer or network, or another module, such as batch size calculation module 218. Ingredient dispensing module 214 associates each predetermined ingredient with a given pump 36, valve 58, or water source 22. Ingredient dispensing module 214 activates or opens pump 36, valve 58, or water source 22 until the predetermined amount has been dispensed. Ingredient dispensing module 214 determines when a predetermined amount has been dispensed by calculating the amount dispensed from inputs from the pumps 36, valves 58, water source 22, flow meters 39, or calibration module 220. Once a predetermined amount has been dispensed, ingredient dispensing module 214 signals to change the status of at least one pumps 36, valves 58, water source 22, nozzle valve 41 to stop dispensing fluid.

In one embodiment, controller 38 includes ingredient changeover module 216. Ingredient changeover module 216 maintains a table associating each pump 36, valve 58, or water source 22 with an ingredient. If a user changes the associated ingredient, the user uses a user interface, external computer, or network to input the new association into ingredient change-over module. In one exemplary embodiment, ingredient changeover module 216 activates purge module 222 to ensure transfer tubing 32 is emptied of the previous ingredient.

Figure 8:
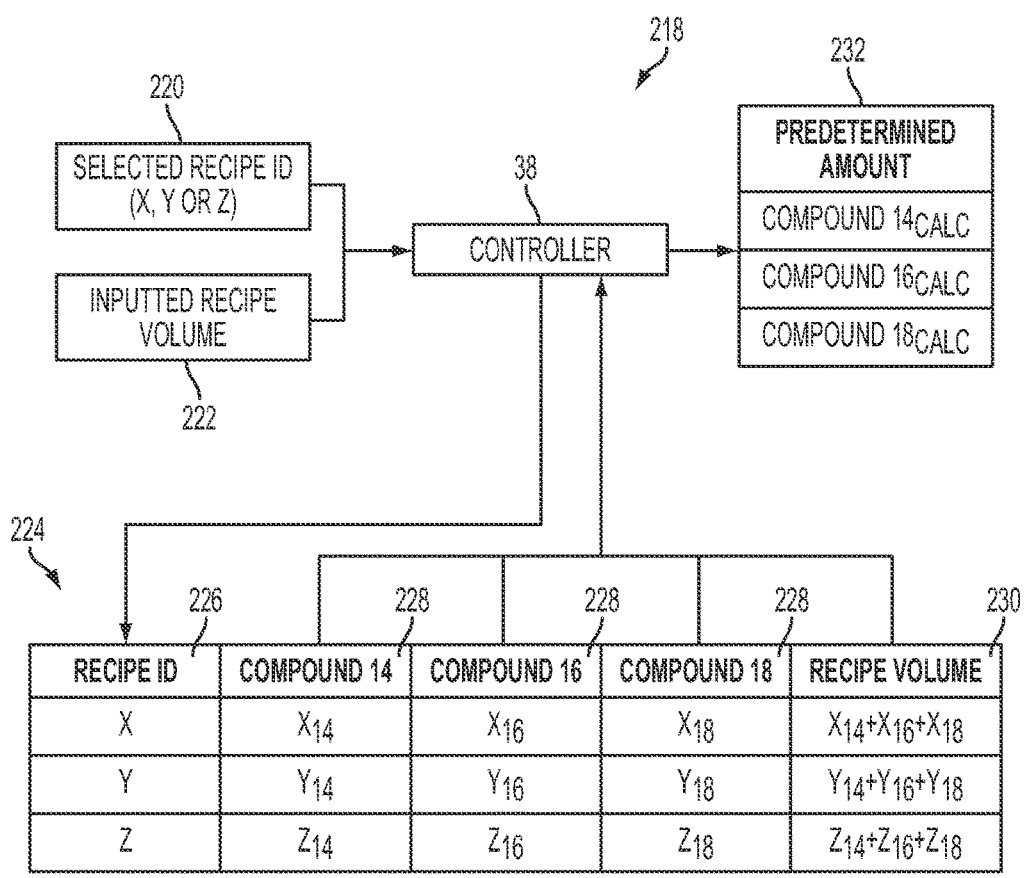
FIG. 8 is a representative view of an exemplary batch size calculation module.

In one embodiment, controller 38 includes batch size calculation module 218. Referring to FIG. 8, a representative view of batch size calculation module 218 is illustrated. Batch size calculation module 218 receives recipe identification 221 and input recipe volume 223. Recipe identification 221 and input recipe volume 223 may be received from a user interface, an external computer, or network or they may be default values stored in memory. Recipe calculation module then associates selected recipe identification 221 with an entry in ingredient table 224. As shown in FIG. 8, selected recipe identification 221 may be one of X, Y, or Z, each of which is associated with an entry in column 226 of table 224. Table 224 includes an ingredient amount in columns 228 for each ingredient in recipe identification 221. As shown in FIG. 8, recipe identification X includes three ingredients, compound 14, compound 16, and compound 18. Although three compounds are shown recipe X in FIG. 8, a recipe may have more or fewer compounds, depending on the application. Recipe X contains amount $X_{14}$ of Ingredient 1, amount $X_{16}$ of Ingredient 2, and amount $X_{18}$ of Ingredient 3. Table 224 also includes a recipe volume, 230, equal to the sum of the amounts of each ingredient, $X_{14}$, $X_{16}$, $X_{18}$. Batch size calculation module 218 uses the ratio of the input recipe volume 223 to recipe volume 230 for the selected recipe ID as a multiplier for the amount of each ingredient $X_{14}$, $X_{16}$, $X_{18}$ to determine the predetermined amount 232 of each ingredient: Compound $14_{calc}$, Compound $16_{calc}$, Compound $18_{calc}$. Predetermined amount 232 may be used by other modules, such as ingredient dispensing module 214.

In one embodiment, controller 38 includes calibration module 220. Calibration module 220 signals controller 38 to open the nozzle valve 41 and pump 36, valve 58, or water source 22 for one nozzle 40 for a predetermined length of time. The predetermined length of time may be received by calibration module 220 from a user interface, an external computer, or network or it may be a default value stored in memory. A user collects and measures the volume of liquid dispensed through dispensing nozzle 40 and inputs the value into a user interface, an external computer, or network. Calibration module 220 then calculates the flow rate by dividing the volume of liquid dispensed by the predetermined time. In one exemplary embodiment, calibration module 220 determines an average flow rate from a plurality of measurements.

In one embodiment, controller 38 includes purge module 222. An operator may purge fluid remaining in the transfer tubing 32 upon start-up of dispenser 10 or if one of vessels 12 is replaced with a vessel containing a new compound. An operator may also purge transfer tubing 32 if air is introduced to transfer tubing 32 during compound change-over or the level of compound 14, 16, 18, 20 drops below transfer tubing inlet 34 during use of dispenser 10. Purge module 222 signals controller 38 to open the nozzle valve 41 and pump 36, valve 58, or water source 22 for one nozzle 40 for a predetermined length of time. The predetermined length of time may be received by purge module 222 from a user interface, an external computer, or network or it may be a default value stored in memory. A user collects the liquid dispensed through dispensing nozzle 40.

While this invention has been described as relative to exemplary designs, the present invention may be further modified within the spirit and scope of this disclosure. Further, this application is intended to cover such departures from the present disclosure as come within known or customary practice in the art to which this invention pertains.

The invention claimed is:

1. A automated media dispenser comprising:
 a plurality of vessels, each vessel containing a liquid compound, wherein at least one vessel is positioned on a stir plate and the at least one vessel further includes a stir bar;
 a dispensing unit including a plurality of nozzles, each of the plurality of vessels being in fluid communication with one of the plurality of nozzles;
 a mixing container having an interior for receiving the liquid compounds; and
 a swing arm supporting the dispensing unit between a first position over the interior of the mixing container and a second position not over the mixing container, the plurality of nozzles positioned over a top opening of the mixing container when the dispensing unit is positioned in the first position;
 wherein an electronic controller dispenses predetermined amounts of at least one of the liquid compounds through one of the plurality of nozzles into the mixing container when the dispensing unit is positioned in the first position.

2. The automated media dispenser of claim 1 further comprising an autoclave or media preparator configured to sterilize the dispensed liquid compounds, wherein the mixing container is a portion of the autoclave or media preparator.

3. The automated media dispenser of claim 1 wherein the electronic controller dispenses a predetermined amount of at least one liquid using at least one pump positioned intermediate the plurality of vessels and the mixing container.

4. The automated media dispenser of claim 3 wherein the at least one pump is a peristaltic pump.

5. The automated media dispenser of claim 3, wherein the electronic controller dispenses a predetermined amount of at least one liquid based on an output from a flow meter operable connected to the controller and positioned between the pump and the mixing container.

6. The automated media dispenser of claim 1 further comprising a positive pressure system attached to at least one vessel and wherein the electronic controller dispenses a predetermined amount of at least one liquid using at least one valve, the valve positioned intermediate the positive pressure system and the mixing container.

7. The automated media dispenser of claim 1 further comprising a water source including a water purification system.

8. The automated media dispenser of claim 7 wherein the electronic controller dispenses a predetermined amount of water into the mixing container from the water source.

9. The automated media dispenser of claim 8 wherein the electronic controller dispenses a predetermined amount of at least one liquid using at least one pump.

10. The automated media dispenser of claim 9 wherein the at least one pump is a peristaltic pump.

11. The automated media dispenser of claim 1, wherein the dispensing unit is configured to move at least one of the plurality of nozzles relative to the plurality of vessels.

12. The automated media dispenser of claim 1, wherein the fluid communication between the plurality of vessels and the plurality of nozzles includes flexible tubing.

* * * * *